(12) United States Patent
Labovitz et al.

(10) Patent No.: US 7,599,051 B1
(45) Date of Patent: Oct. 6, 2009

(54) CALIBRATION OF A SUBSTRATE INSPECTION TOOL

(75) Inventors: Steven M. Labovitz, Sunnyvale, CA (US); Weston L. Sousa, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 394 days.

(21) Appl. No.: 11/562,374

(22) Filed: Nov. 21, 2006

(51) Int. Cl.
*G01N 21/00* (2006.01)
*G01D 18/00* (2006.01)
*G06F 17/50* (2006.01)

(52) U.S. Cl. .............. 356/237.2; 356/237.4; 356/394; 702/85; 703/2

(58) Field of Classification Search ... 356/237.1–237.6, 356/243.1, 243.4, 243.6, 243.8, 394; 364/578, 364/468.17, 468.28; 703/2, 13; 702/85, 702/90–91; 250/372
See application file for complete search history.

(56) References Cited

U.S. PATENT DOCUMENTS

| | | | | |
|---|---|---|---|---|
| 4,636,073 | A * | 1/1987 | Williams | 356/243.4 |
| 5,164,794 | A * | 11/1992 | Markle | 356/394 |
| 5,362,591 | A * | 11/1994 | Imai et al. | 430/5 |
| 5,383,018 | A * | 1/1995 | Sadjadi | 356/243.4 |
| 5,453,830 | A * | 9/1995 | Greed, Jr. | 356/243.4 |
| 5,886,909 | A * | 3/1999 | Milor et al. | 716/4 |
| 6,327,555 | B1 * | 12/2001 | Shimizu et al. | 703/12 |
| 6,509,564 | B1 * | 1/2003 | Suzuki et al. | 250/310 |
| 6,654,698 | B2 * | 11/2003 | Nulman | 702/85 |
| 7,426,031 | B2 * | 9/2008 | Kim et al. | 356/392 |

OTHER PUBLICATIONS

F1620-96 "Standard Practice for Calibrating a Scanning Surface Inspection System Using Monodisperse Polystyrene Latex Spheres Deposited on Polished or Epitaxial Wafer Surface" (Withdrawn Standard 2003), ASTM International, 2003.
George W. Mulholland et al., "Modeling, Measurement, and Standards for Wafer Inspection", published in proceedings of the *Government Microcircuits Applications and Critical Technologies (GOMACTech) Conference: "Countering Asymmetric Threats"*, held Mar. 31 to Apr. 3, 2003 in Tampa, Florida.
William H. Broadbent et al., "Results from a New Reticle Defect Inspection Platform", *23rd Annual BACUS Symposium on Photomask Technology, Proceeding of SPIE*, vol. 5256, pp. 474-488 (2003).
Stan Stokowski et al., "Wafer Inspection Technology Challenges for ULSI Manufacturing—Part I", Spring 1999, Yield Management Solutions, pp. 28-32.

* cited by examiner

*Primary Examiner*—Sang Nguyen
(74) *Attorney, Agent, or Firm*—Joshua D. Isenberg; JDI Patent

(57) ABSTRACT

A method for calibration of a substrate inspection tool is disclosed. The tool is used to inspect a standard substrate having simulated contamination defects with known characteristics. Performance of the tool in detecting the simulated contamination defects is determined. The tool exposes the standard substrate and simulated contamination defects to radiation having a wavelength of about 260 nanometers or less. The simulated contamination defects are stable over time under exposure to radiation having a wavelength of about 260 nanometers or less.

39 Claims, 4 Drawing Sheets

CALIBRATION OF A SUBSTRATE INSPECTION TOOL

FIELD OF THE INVENTION

This invention generally relates to a calibration of a substrate inspection tool and more particularly to a contamination-mode calibration.

BACKGROUND OF THE INVENTION

Substrate processing, e.g., semiconductor wafer fabrication, often requires that substrates be substantially free of defects. Defect detection systems are often employed as part of the manufacturing process to locate defects on a substrate. Certain types of defect detection systems may be calibrated using a deposition of polystyrene latex (PSL) spheres as a known source of scatter signal. Radiation is directed toward a calibration sample substrate having PSL spheres of a known size distribution deposited on its surface. The measured amplitude of radiation scattered by the PSL spheres may be used as a standard for matching the response of a defect detection system to a known source of scattering. The use of a deposition of polystyrene latex (PSL) spheres as a known source of scatter signal allows meaningful comparisons to be made between scatter signals from PSL spheres as measured by bright or dark field detection scanning surface inspection systems of different designs. The measured PSL scatter signal amplitude may be compared to scatter signals for a sample substrate having real surface defects whose identity and true size are unknown. This practice provides a basis for quantifying system performance as used in related standards concerned with parameters such as sensitivity, repeatability and capture rate.

As the size of semiconductor integrated circuit features decreases detection of smaller and smaller defects becomes more critical. As a result, shorter wavelength radiation may be used to detect smaller defects. Given this requirement a defect detection system may expose a PSL calibration target to radiation 257 nanometers or shorter wavelength radiation. Such radiation has been observed to degrade conventional polystyrene latex (PSL) spheres used to calibrate surface inspection systems. This can lead to additional cost and downtime associated with recoating or replacement of a PSL calibration target.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Embodiments of the present invention utilize simulated contamination defects that are stable over time under exposure to ultraviolet radiation for calibration of a substrate inspection tool. Calibration of a defect detection system is largely a matter of exposing the simulated defects on the surface of the substrate to radiation having a wavelength that is sufficiently short to be significantly scattered by the simulated defects. The amplitude of the radiation scattered by the simulated defects is measured and associated with a nominal size of the simulated defects. Calibration using the simulated defects may be performed, e.g., as described in ASTM standard: F1620-96, "Standard Practice for Calibrating a Scanning Surface Inspection System Using Monodisperse Polystyrene Latex Spheres Deposited on Polished or Epitaxial Wafer Surfaces", (Withdrawn 2003), ASTM International, 2003, which is incorporated herein by reference.

After calibration, the system may then be used to measure scattering signals from localized light scatterers on a test substrate. The scattering signal may be expressed in terms of a latex sphere equivalent (LSE), which refers to the diameter of a monodisperse polystyrene latex sphere that produces the same detected scattering intensity as the localized light scatterer (LLS) under investigation under identical test conditions.

Figure 1:
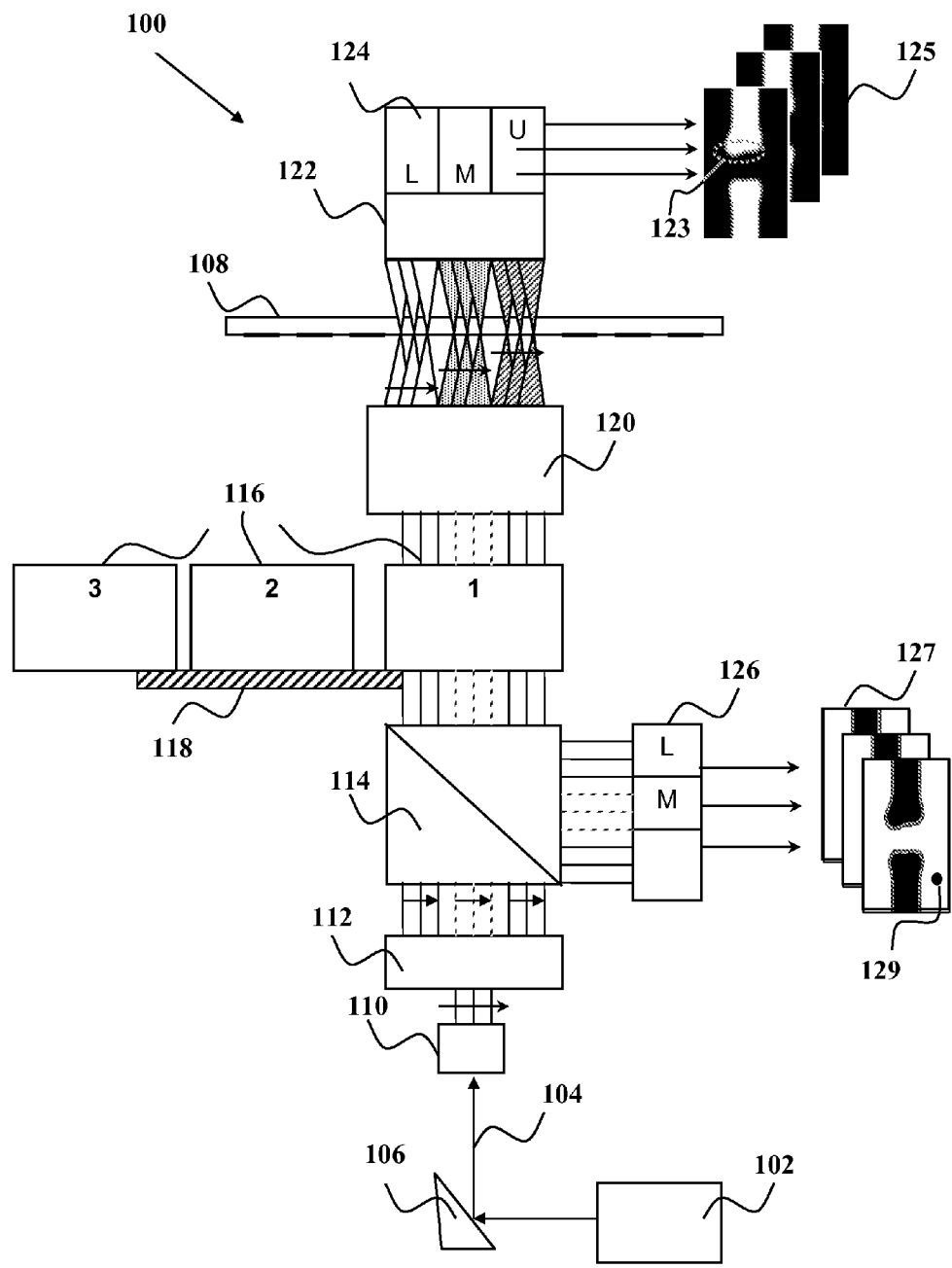
FIG. 1 is a vertical cross-section schematic diagram of a sample inspection system that may be used in embodiments of the present invention.

By way of example FIG. 1 is a schematic view of a scanning surface inspection system (SSIS) 100 illustrating an example of a general set up for a sample inspection system that may be used with embodiments of the present invention. By way of example, the system 100 may be a bright field imaging system, such as a TeraStar™ Scanned Beam Reticle Inspection System, commercially available from KLA-Tencor Corporation of San Jose, Calif. In addition, embodiments of the present invention may be used in conjunction with other bright field imaging system designs, such as a TeraScan™ DUV Reticle Inspection System available from KLA-Tencor Corporation of San Jose, Calif. An example of such an alternative implementation is described below with respect to FIG. 4. In addition, certain embodiments of the present invention may also be used with so-called "dark field" inspections systems, sometimes called surface scanning inspection systems (SSIS's). Examples of dark field inspection systems include, but are not limited to model AIT, Puma 9000 and Puma 9100 wafer inspection systems from KLA-Tencor Corporation.

In the system 100, a radiation source 102 may provide incident radiation 104 at one or more wavelengths in a wide electromagnetic spectrum (including but not limited to ultraviolet, visible, infrared and the like). The radiation source 102 may be a laser providing the incident radiation 104 in the form of a laser beam. A beam steering mechanism 106 and other optical components may steer the incident radiation 104 such that the incident radiation 104 is normally incident on a substrate 108 such as a wafer, mask or reticle. The substrate 108 may be mounted to a stage that allows for indexing and scanning of the substrate. In some embodiments of the present invention, the substrate 108 may be a pattern defect substrate. In other embodiments, simulated contamination defects UV-resistant nanoparticles may be disposed on a surface of the substrate 108.

Additional optical components may be disposed between the beam steering mechanism 106 and the substrate 108. For example an acoustic scanner 110 may separate the incident radiation into multiple beams. A beam replicator 112 may replicate each of these beams in different wavelength ranges. The replicated beams may optionally pass through an optical circulator 114 and one or more pixel filters 116. The pixel filter 116 is an optical subsystem that creates various pixel sizes. Smaller pixels are used to achieve sensitivity for smaller defects. In some systems, multiple filters 116 may be mounted to a turret 118 for quick replacement. Alternatively, different pixel sizes may be obtained through use of a zoom lens system. After passing through the pixel filters 116, the replicated beams are focused by an imaging objective 120 onto a surface of the substrate 108. Collection optics 122 mounted on opposite the objective 120 may collect radiation transmitted by the substrate 108 and couple the transmitted radiation to photosensors 124. Signals from the photosensors 124 can be used to generate images 125 of the substrate 108 from the detected transmitted radiation. Radiation reflected by the substrate may be collimated by the imaging objective 120 and deflected by the optical circulator 114 to another set of photosensors 126. Signals from the photosensors 126 can be used to generate images 127 of the substrate 108 from the detected transmitted radiation. In a pattern defect mode, the system 100 may detect malformations in a mask pattern on the substrate 108 from the images 125 obtained using transmitted light or the images 127 obtained using reflected light, but not both simultaneously. The pattern defect mode is used with a pattern defect substrate having a simulated mask pattern with simulated defects at known locations. The pattern defect mode is used to detect defects 123 in a mask pattern, e.g., missing parts of the pattern or relatively large defects in the pattern that are attached to or close to other parts of the pattern. In a contamination mode of the system 100, contaminants on the surface of the substrate 108 may be detected by comparing the images 125 and 127. For example, a feature 129 appearing in image 127 but not in image 125 may be marked as a contaminant.

Figure 2:
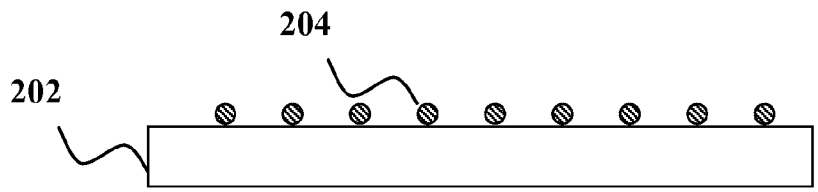
FIG. 2 is a cross-sectional schematic diagram of a standard substrate coated with nanoparticles according to an embodiment of the present invention.

By way of example, a calibration standard may use simulated defects in the form of UV-resistant nanoparticles. Such UV-resistant nanoparticles may be used to calibrate both bright field and dark field inspection tools. There are a number of different ways of producing simulated defects that are resistant to radiation having a wavelength of about 260 nanometers or less. FIG. 2 is a cross-sectional schematic diagram of a standard substrate coated with nanoparticles according to an embodiment of the present invention. As shown in FIG. 2, a substrate 202 is coated with nanoparticles 204. The nanoparticles 204 are made of a material that is stable over time under exposure to radiation having a wavelength of about 260 nanometers or less. The nanoparticles 204 may be deposited on a surface of substrate 202 using the same methodology currently employed for polystyrene latex (PSL) spheres. Specifically, a dilute suspension of the nanoparticles 204 without a surfactant may be sprayed using an apparatus that applies a specific range of particles sizes to a surface of the substrate 202. The nanoparticles 204 may be characterized by a size distribution having a mean size µ equal to about 250 nanometers or less, preferably between 50 nanometer and 155 nanometer, and a standard deviation σ less than or equal 10 nanometer. By way of example, and without loss of generality, the nanoparticles 204 may have a mean diameter µ of about 60 nanometers and a standard deviation σ of about 4 to 8 nanometers.

Particles of a desired size distribution may be obtained commercially. Alternatively, the system used to deposit the nanoparticles may select particles in a certain narrow size range from a nanoparticle dispersion having a broader range of particle sizes. By way of example, the deposition system may include a differential mobility analyzer (DMA) to perform the size selection. An example of the use of a differential mobility analyzer for this purpose is set forth by George W. Mulholland et al. in "Modeling, Measurement, and Standards for Wafer Inspection", published in the proceedings of the *Government Microcircuits Applications and Critical Technologies (GOMACTech) Conference: "Countering Asymmetric Threats,"* held Mar. 31 to Apr. 3, 2003 in Tampa, Fla. A DMA may include an inner cylindrical tube of outside radius $r_1$ connected to a variable high voltage DC power supply and an outer annular tube of inside radius $r_2$ connected to ground. Clean sheath air flows through an axial region between the inner tube and the inner surface of the outer tube, while the charged aerosol enters this region through an axisymmetric opening in the outer tube. The positively charged nanoparticles move radially towards the center rod under the influence of an electric field. Near the bottom of the classifying region, a fraction of the air flow containing a near-monodisperse aerosol of the nanoparticles exits through a slit in the center tube. The quantity measured by the DMA is the electrical mobility, $Z_p$, defined as the velocity a particle attains under a unit electric field. The electrical mobility may be expressed as:

$$Z_p = \frac{Q_c}{2\pi V L}\ln(r_2/r_1) \qquad \text{(Eq. 1)}$$

Where V is a voltage applied between the inner and outer tubes, $Q_c$ is a sheath air flow rate and L is a length of the central tube down to the slit. This equation is valid provided the sheath air flow, $Q_c$, is equal to an excess flow, $Q_m$, leaving the classifier. A transfer function may be derived from Eq. 1. The transfer function may be defined as the probability that a particle will leave the sampling slit. The transfer function is of great importance, because the monodisperse concentration exiting the DMA is proportional to the convolution of the transfer function with the particle size distribution function. The transfer function has a triangular shape with a value of 1 when the voltage at which the computed particle mobility using the equation above is equal to the mobility of the particle. The ratio of the base of the transfer function triangle in terms of voltage divided by the peak voltage is predicted to be $2(Q_s/Q_c)$, where $Q_s$ is the flow of monodisperse aerosol. From this one can see that the smaller the flow ratio the more monodisperse is the aerosol leaving the classifier. A relationship between electrical mobility $Z_p$ and particle size $D_p$ may be obtained by equating the electric field force of a singly charged particle with the Stokes friction force. According to this relationship:

$$Z_p = \frac{eC(D_p)}{3\pi\mu D_p} \qquad \text{(Eq. 2)}$$

where μ is the dynamic viscosity of air, and e is the electron charge and C(Dp) is the Cunningham slip correction, which corrects for non-continuum gas behavior on the motion of small particles. By equating Eq. 1 and Eq. 2 it may be seen that if L, $r_1$ and $r_2$ are fixed, the size of particles in the monodisperse aerosol exiting the in inner tube may be selected by appropriately adjusting V and $Q_C$.

The nanoparticles 204 may be manufactured from a material having suitable resistance to degradation by ultraviolet radiation. The nanoparticles 204 may include ceramic or elemental nanoparticles. The nanoparticles 204 can be made of a ceramic, e.g., an oxide such as alumina, niobia, titania, zirconia or iron oxide ceramic. Alternatively, the nanoparticles may be made of a non-oxide ceramic, e.g., a silicide, nitride, carbide and the like. The nanoparticles 204 also can be made of one or more metals, which are characterized by a single valance state such as silicon and zirconium, or a ceramic containing one or more such metals. The substrate 202 may be any suitable substrate for a calibration standard, e.g., patterned or un-patterned wafer or photo-mask.

The use of ceramic or elemental nanoparticles 204 gives the same performance on the substrate 202 as polystyrene latex (PSL) spheres with a longer lifetime than polystyrene latex (PSL) spheres. The degradation of polystyrene latex (PSL) spheres results when polystyrene latex (PSL) spheres is exposed to the radiation having the wavelength less than 260 nanometers. The high energy photons break the polymer chains, thus the polystyrene latex (PSL) spheres will physically shrink. Bond strengths in ceramics and elemental materials are substantially higher than bond strengths of polystyrene latex (PSL) spheres, and therefore more resistant to degradation by exposure to the radiation than polystyrene latex (PSL) spheres of the same size range. Zirconia is a most preferable material because of its ease of deposition and the single valance state of zirconium. Zirconia ($ZrO_2$) nanopowder is available commercially, e.g., as product number 544760 from Sigma Aldrich, Corporation of St. Louis, Mo.

The standard substrate 202 coated with nanoparticles 204 may be exposed to radiation of a known wavelength of about 260 nanometers or less during calibration of an inspection tool. An amplitude of scattering of the radiation by the nanoparticles is measured with the inspection tool. The measured scattering of the radiation of the nanoparticles may be associated with a nominal size of the nanoparticles 204.

Figure 3A:
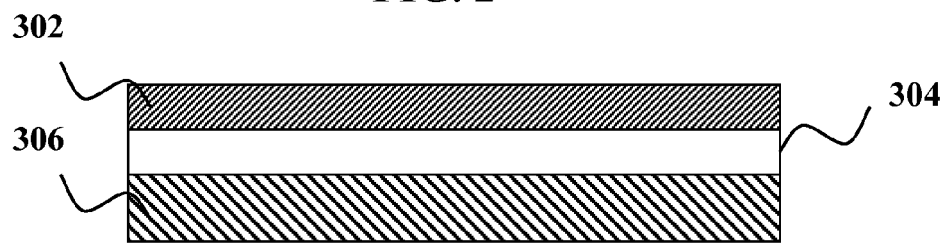
FIGS. 3A-3D are cross-sectional schematic diagrams illustrating the steps of making a pattern defect substrate that may be used for contamination-mode calibration of an inspection tool according to embodiments of the present invention.

According to another embodiment of the present invention, the standard substrate may be a pattern defect substrate that may be used for a contamination-mode calibration of the inspection tool 100. An example of a commercially available pattern defect substrate is a SPICA200 pattern defect mask available from KLA-Tencor Technologies of San Jose, Calif. FIGS. 3A-3D are cross-sectional schematic diagrams illustrating a pattern defect substrate at various stages of manufacture. FIG. 3A illustrates a starter material for making of a pattern defect substrate, which includes a phase shift layer 304 disposed between an opaque layer 302 and an optically transmissive substrate 306. The opaque layer 302 may be made of chrome. The phase shift layer 304 may be made of molybdenum silicide (MoSi) or chromium fluoride (CrF). The phase shift layer 304 may be made of or may contain a material having optical properties that are similar to those of common contaminants. Examples of optical properties that drive defect detection include, but are not limited to index of refraction and dielectric constant. Examples of classes of materials with optical properties similar to common contaminants include, but are not limited, to sulfates, e.g., ammonium sulfates, oxalates and possibly carbamates.

The optically transmissive substrate 306 may be made of quartz. The optically transmissive substrate 306 can be a photomask blank. Simulated defects may be patterned into the opaque layer 302 and/or the phase shift layer 304 using a pattern generator, e.g. e-beam or laser. These defects may be defined in a database used to create the mask, and therefore their number, location and size may be well controlled. In addition such simulated defects may be easily sized, e.g., using a Critical Dimension—Scanning Electron Microscopy (CD-SEM). Fabrication of such masks for contamination mode calibration requires no changes to existing pattern defect mask design. However, calibrating a contamination mode of an inspection tool with a pattern defect mask is an entirely new usage for pattern defect masks. In addition, the use of a pattern defect mask for contamination mode calibration is somewhat counterintuitive since the type of defects that best simulate contamination, e.g., defects that are relatively small and not attached to simulated pattern geometry, would not normally be identified as pattern defects in pattern defect mode.

Figure 3B:
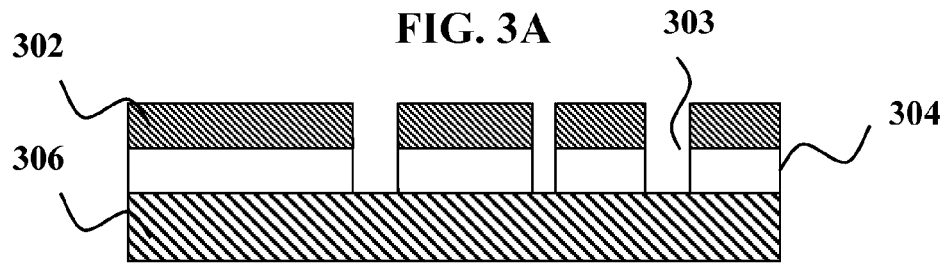
Figure 3C:
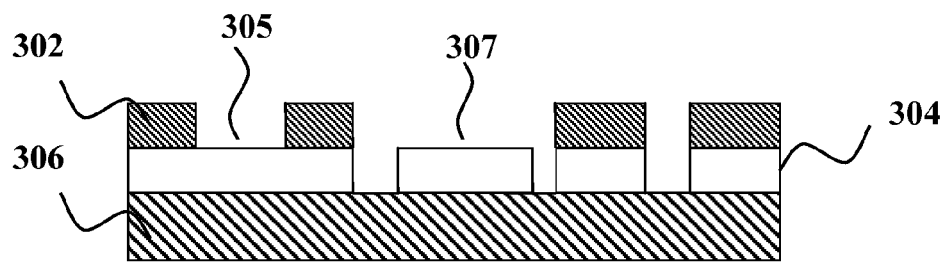

FIG. 3B illustrates a step of making holes 303 through the opaque layer 302 and the phase shift layer 304, exposing some portions of the substrate 306. FIG. 3C illustrates a step of removing some portions 305 and 307 of the opaque layer 302, exposing some portions of the phase shift layer 304.

Figure 3D:
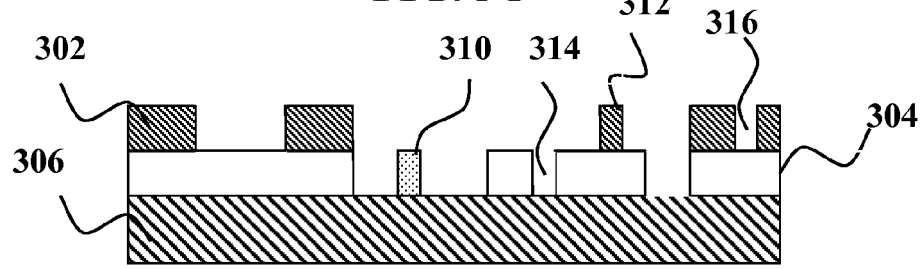

FIG. 3D shows a step of making simulated defects in the opaque layer 302 and the phase shift layer 304. As shown in FIG. 3D, the simulated defects may include a small piece of phase shift layer material 310 on an exposed portion of the substrate 306, a small piece of opaque layer material 312 on an exposed portion of the phase shift layer 304, a small hole 314 in the phase shift layer 304 that exposes a portion of the substrate 306, and a small hole 316 in the opaque layer 302 that exposes a portion of the phase shift layer 304. In addition, the small piece of phase shift layer material 310 may be modified, e.g., by oxidizing or ion implanting to change its optical properties. Such simulated pattern defects can have a substantially longer lifetime under prolonged UV exposure than PSL spheres. In addition, control of the size and location of the defects can be made much more precise using simulated defects formed in a pattern defect substrate.

Figure 4:
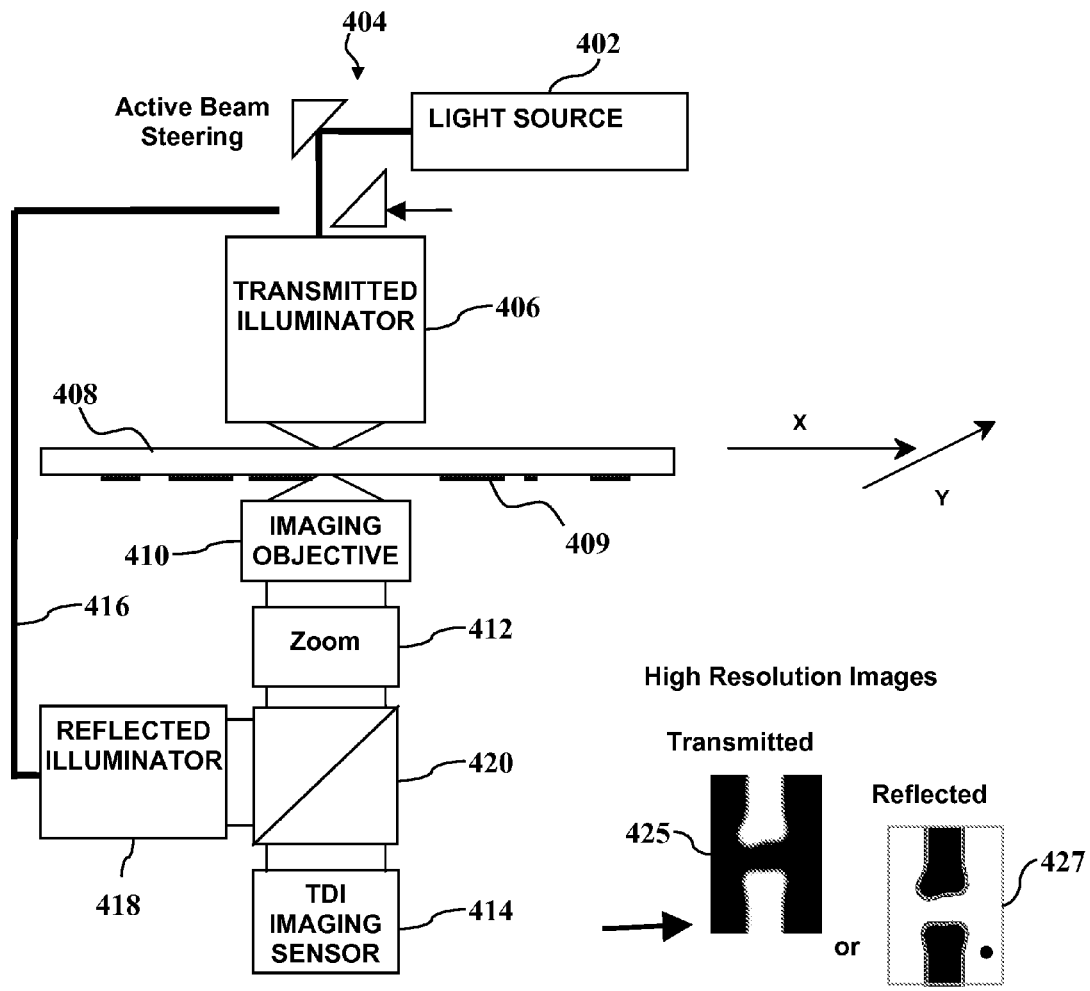
FIG. 4 is a schematic diagram illustrating an example of contamination mode calibration using a pattern defect substrate according to an embodiment of the present invention.

FIG. 4 is a schematic diagram illustrating an example of contamination mode calibration using pattern defect substrate as described in FIGS. 3A-3D according to an embodiment of the present invention. Specifically, FIG. 4 illustrates a schematic view of a bright field reticle inspection system 400. By way of example, the system 400 may be a TeraScan™ DUV Reticle Inspection System available from KLA-Tencor Corporation of San Jose, Calif. Such a system is described in detail, e.g., by William H. Broadbent et al, in "Results from a new reticle defect inspection platform" in 23*rd Annual BACUS Symposium on Photomask Technology, Proceedings of the SPIE*, Volume 5256, pp. 474-488 (2003), which is incorporated herein by reference. The system 400 may use a high resolution microscope and linear sensor architecture, as opposed to the multi-beam laser scanner architecture of the system 100 of FIG. 1. Such an architecture offers several advantages to the laser scanner which include the potential for higher speed and no beam crosstalk.

The system includes an illumination source 402. By way of example, the illumination source 402 may be a 257-nm wavelength continuous wave (CW) laser. An active beam steering subsystem 404 compensates for beam drift and may also reduce replacement time for the light source 402. A transmitted light illuminator 406 may have several different configurations that can be selected by a user at run-time. For example one configuration may implement standard contrast for binary and EPSM reticles. Another configuration may implement phase contrast for quartz etch reticles such as alternating, chromeless, and the like. The phase contrast mode may provide improved imaging contrast to quartz phase defects (bumps and divots) allowing higher defect sensitivity.

A substrate 408 that is to be inspected is placed between the transmitted illuminator 406 and an imaging objective 410. In embodiments of the invention, the inspection system 400 may be used for contamination mode calibration, therefore substrate 408 may be a pattern defect substrate. In this example, the surface of the substrate 408 that includes a reticle pattern 409 faces the imaging objective 410. The substrate 408 may be scanned, e.g., using an air bearing stage. The reticle may be scanned along a first axis X for continuous image pick-up, and then indexed along a second axis Y after each swath to provide a serpentine inspection path.

The objective 410 images the reticle surface 409 through a zoom lens 412 onto an imaging sensor 414. The zoom lens 412 allows different pixel sizes to be selected by the user at run-time providing different defect sensitivities and associated scan times. Pixel sizes may be of any suitable size including, but not limited to, e.g., 72-nm, 90-nm, 125-nm and 150-nm pixel sizes. By way of example, the imaging sensor 414 may be a time-domain-integration (TDI) sensor. Such a sensor design offers high speed continuous image pick-up at much lower light levels than a conventional charge coupled device (CCD) linear sensor.

The system 400 also includes a reflected illumination optical path 416 which may be used during defect review to aid in the correct classification of contamination. Radiation may be coupled from the source 402 to the surface 409 of the substrate 408 via the reflected illumination optical path 416, a reflected illuminator 418 and a beamsplitter 420. The image sensor 414 may thus produce high resolution images 425 and 427 respectively showing transmitted and reflected images of portions of the substrate 408.

Figure 5:
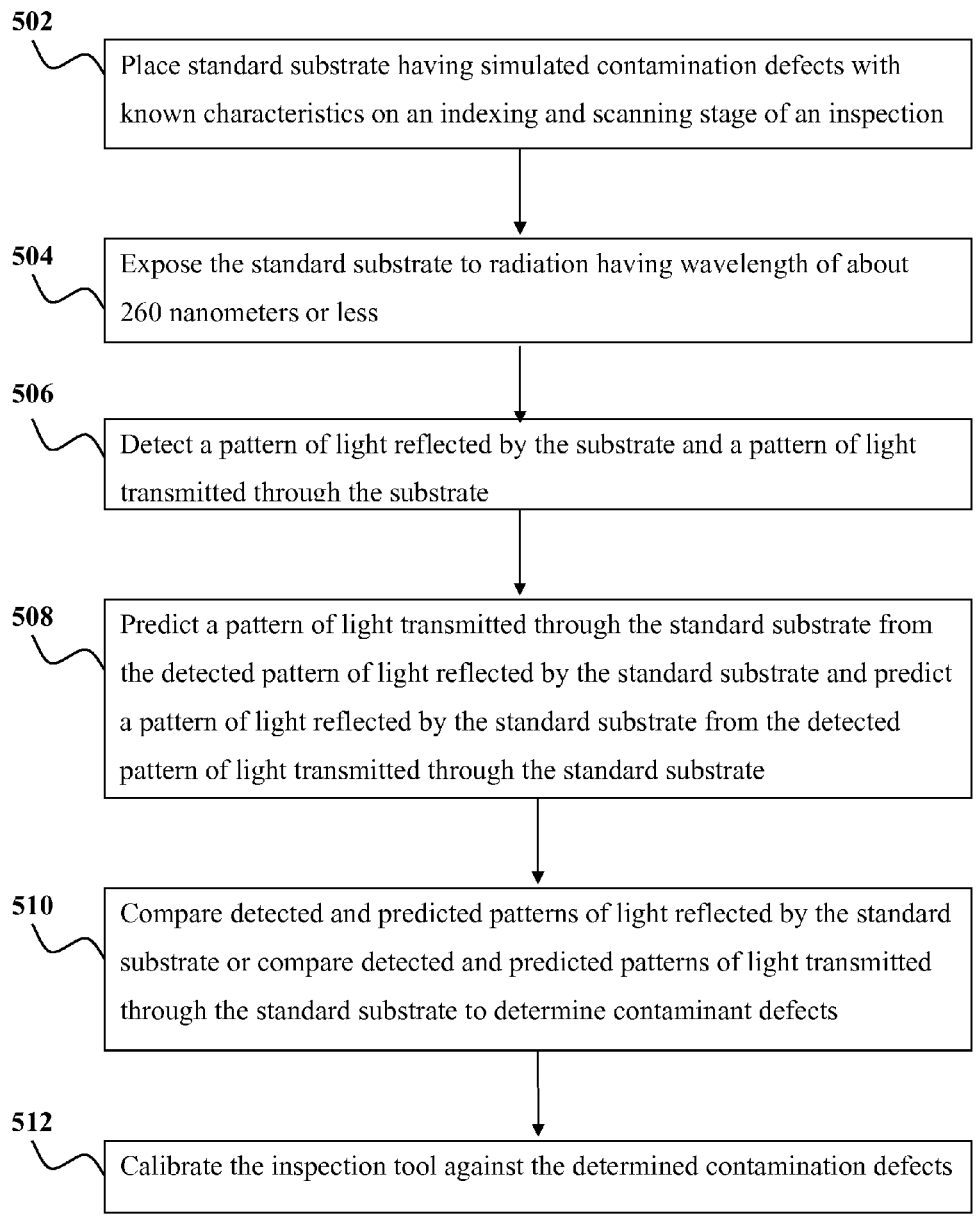
FIG. 5 is a flow diagram illustrating an example of contamination mode calibration using a pattern defect substrate according to an embodiment of the present invention.

FIG. 5 is a flow diagram illustrating a method for contamination mode calibration using a pattern defect substrate according to an embodiment of the present invention. A standard substrate having simulated contamination defects with known characteristics is placed on an indexing and scanning stage of an inspection tool, which is shown in step 502. By way of example, the inspection tool may be a bright field system, e.g., as shown in FIG. 1 or a bright field system, e.g., as in FIG. 4. In some embodiments, a dark field system may be used as the inspection tool. The pattern defect substrate is exposed to radiation having a wavelength of about 260 nanometers or less, which is shown in step 504. The simulated defects on the standard substrate are stable over time under exposure to the radiation. The inspection tool detects a pattern of light reflected by the substrate and a pattern of light transmitted through the substrate, which is shown in steps 506. A pattern of light transmitted through the standard substrate is predicted from the detected pattern of light reflected by the substrate, and a pattern of light reflected by the standard substrate is predicted from the detected pattern of light transmitted through the standard substrate, which is shown in step 508. The contaminant defects are determined by comparing the detected and predicted patterns of light reflected by the standard substrate or by comparing the detected and predicted patterns of light transmitted through the standard substrate, which is shown in step 510. The inspection tool is then calibrated against the determined contaminant defects, which is shown in step 512. The performance of the tool may be determined, e.g., by ascertaining whether the tool is able to locate simulated defects at known locations, or is able to accurately characterize properties of the simulated defects, e.g., their size distribution, when these properties are known.

Embodiments of the present invention allow for calibration of inspection tools with standards that last longer. This reduces the cost and lost productivity associated with having to frequently replace and/or recoat the calibration standard.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for calibration of a substrate inspection tool, comprising:

using the tool to inspect a standard substrate having simulated contamination defects with known characteristics, wherein the tool exposes the standard substrate and simulated contamination defects to radiation having a wavelength of about 260 nanometers or less;

determining the simulated contamination defects with the tool by comparing a detected pattern of radiation reflected by the standard substrate to a predicted pattern or by comparing the detected pattern of radiation transmitted through the standard substrate and a predicted pattern; and calibrating the tool against the determined simulated contamination defects;

wherein the simulated contamination defects are stable over time under exposure to radiation having a wavelength of about 260 nanometers or less.

2. The method of claim 1 wherein the simulated contamination defects include ceramic or elemental nanoparticles disposed on a surface of the substrate, wherein the nanoparticles are characterized by a size distribution having a mean size $\mu$ and a standard deviation $\sigma$, wherein $\mu$ is less than or equal to about 250 nanometers and $\sigma$ is less than or equal to about 10 nanometers.

3. The method of claim 2, wherein the nanoparticles are made of an oxide ceramic.

4. The method of claim 3 wherein the oxide ceramic is an alumina, niobia, titania, zirconia or iron oxide ceramic.

5. The method of claim 2 wherein the nanoparticles are made of one or more metals or an oxide of the one or more metals.

6. The method of claim 5 wherein the one or more metals are characterized by a single valence state.

7. The method of claim 5 wherein the one or more metals includes zirconium.

8. The method of claim 2 wherein the substrate is a test mask.

9. The method of claim 2 wherein the substrate is a test wafer.

10. The method of claim 2 wherein $\mu$ is between about 50 nanometers and about 155 nanometers.

11. The method of claim 2 wherein disposing the ceramic or elemental nanoparticles on the surface of the substrate includes, diluting the nanoparticles in a solvent without a surfactant.

12. The method of claim 2 wherein using the ceramic or elemental nanoparticles as a contamination standard includes:
exposing the nanoparticles on the surface of the substrate to radiation of a known wavelength;
measuring an amplitude of scattering of the radiation by the nanoparticles with the inspection tool; and
associating measured scattering of the radiation with a nominal size of the nanoparticles.

13. The method of claim 12 wherein using the ceramic or elemental nanoparticles as a contamination standard further includes:
exposing a test substrate to radiation of the known wavelength;
measuring an amplitude of scattering of the radiation by one or more localized scattering defects on the test substrate with the inspection tool; and
comparing the amplitude of measuring an amplitude of scattering of the radiation by one or more localized scattering defects to an amplitude of scattering of the radiation by the nanoparticles with the inspection tool.

14. The method of claim 2 wherein the nanoparticles are more resistant to degradation by exposure to the radiation than polystyrene latex (PSL) nanoparticles of the same size range.

15. The method of claim 2 wherein the substrate inspection tool includes a dark field substrate inspection system.

16. The method of claim 15 wherein the pattern defect substrate includes one or more simulated contamination defects of known size and location.

17. The method of claim 15 wherein inspecting the standard substrate in a contamination detection mode includes:
exposing the sample substrate to light;
detecting a pattern of light reflected by the substrate
detecting a pattern of light transmitted through the substrate;
predicting a pattern of light transmitted through the substrate from the detected pattern of light reflected by the substrate;
predicting a pattern of light reflected by the substrate from the detected pattern of light transmitted through the substrate; and
determining whether any contaminants are present on the substrate by comparing the detected pattern of transmitted light to the predicted pattern of transmitted light and/or by comparing the detected pattern of reflected light to the predicted pattern of reflected light.

18. The method of claim 16 wherein the phase shift layer contains a material having optical properties similar to optical properties of photo-induced contamination defects.

19. The method of claim 16 wherein the contamination defect mask includes one or more simulated defects in the opaque layer and/or the phase shift layer on the substrate.

20. The method of claim 16, where in the phase shift layer includes molybdenum silicide or chromium fluoride.

21. The method of claim 18 wherein the one or more simulated defects include a small piece of phase shift layer material on an otherwise exposed portion of the substrate, a small piece of opaque layer material on an otherwise exposed portion of the phase shift layer, a small hole in the phase shift layer that exposes a portion of the substrate or a small hole in the opaque layer that exposes a portion of the phase shift layer.

22. The method of claim 1 wherein the standard substrate is a pattern defect substrate and wherein using the tool to inspect the standard substrate includes inspecting the standard substrate in a contamination detection mode.

23. The method of claim 22 wherein the contamination defect mask includes a phase shift layer disposed between an opaque layer and an optically transmissive substrate.

24. The method of claim 1 wherein the substrate inspection tool includes a bright field reticle inspection system.

25. A method for using of a substrate inspection tool, comprising:
using the tool to inspect a standard substrate having simulated contamination defects with known characteristics, wherein the tool exposes the standard substrate and simulated contamination defects to radiation having a wavelength of about 260 nanometers or less;
determining a performance of the tool in detecting the simulated contamination defects; wherein the simulated contamination defects are stable over time under exposure to radiation having a wavelength of about 260 nanometers or less;
using the tool to measure an amplitude of scattering of the radiation by one or more localized scattering defects on a test substrate;
comparing the amplitude of scattering of the radiation by one or more localized scattering defects to an amplitude of scattering of the radiation of the simulated contaminant defects of the standard substrate; and
calibrating the tool against the amplitude of scattering of the radiation of the simulated contaminant defects.

26. The method of claim 25 wherein the simulated contamination defects include ceramic or elemental nanoparticles disposed on a surface of the substrate, wherein the nanoparticles are characterized by a size distribution having a mean size $\mu$ and a standard deviation $\sigma$, wherein $\mu$ is less than or equal to about 250 nanometers and $\sigma$ is less than or equal to about 10 nanometers.

27. The method of claim 26, wherein the nanoparticles are made of an oxide ceramic.

28. The method of claim 27 wherein the oxide ceramic is an alumina, niobia, titania, zirconia or iron oxide ceramic.

29. The method of claim 26 wherein the nanoparticles are made of one or more metals or an oxide of the one or more metals.

30. The method of claim 29 wherein the one or more metals are characterized by a single valence state.

31. The method of claim 29 wherein the one or more metals includes zirconium.

32. The method of claim 26 wherein the substrate inspection tool includes a dark field substrate inspection system.

33. The method of claim 25 wherein the standard substrate is a pattern defect substrate and wherein using the tool to inspect the standard substrate includes inspecting the standard substrate in a contamination detection mode.

34. The method of claim 33 wherein the pattern defect substrate includes one or more simulated contamination defects of known size and location.

35. The method of claim 34 wherein the phase shift layer contains a material having optical properties similar to optical properties of photo-induced contamination defects.

36. The method of claim 35 wherein the one or more simulated defects include a small piece of phase shift layer material on an otherwise exposed portion of the substrate, a small piece of opaque layer material on an otherwise exposed portion of the phase shift layer, a small hole in the phase shift layer that exposes a portion of the substrate or a small hole in the opaque layer that exposes a portion of the phase shift layer.

37. The method of claim 34 wherein the contamination defect mask includes one or more simulated defects in the opaque layer and/or the phase shift layer on the substrate.

38. The method of claim 33 wherein the pattern defect mask includes a phase shift layer disposed between an opaque layer and an optically transmissive substrate.

39. The method of claim 25 wherein the substrate inspection tool includes a bright field reticle inspection system.

* * * * *